US010531939B2

(12) United States Patent
Stotland

(10) Patent No.: US 10,531,939 B2
(45) Date of Patent: Jan. 14, 2020

(54) INTERDENTAL ANCHORING APPARATUSES AND METHODS

(71) Applicant: Mitchell A. Stotland, Norwich, VT (US)

(72) Inventor: Mitchell A. Stotland, Norwich, VT (US)

(*) Notice: Subject to any disclaimer, the term of this patent is extended or adjusted under 35 U.S.C. 154(b) by 670 days.

(21) Appl. No.: 15/071,152

(22) Filed: Mar. 15, 2016

(65) Prior Publication Data

US 2017/0265975 A1    Sep. 21, 2017

(51) Int. Cl.
| | |
|---|---|
| *A61C 5/80* | (2017.01) |
| *A61C 15/00* | (2006.01) |
| *A61B 1/00* | (2006.01) |
| *A61F 5/058* | (2006.01) |
| *A61F 5/56* | (2006.01) |
| *A61M 16/04* | (2006.01) |

(52) U.S. Cl.
CPC .......... *A61C 15/00* (2013.01); *A61B 1/00147* (2013.01); *A61F 5/05891* (2013.01); *A61F 5/566* (2013.01); *A61M 16/0497* (2013.01)

(58) Field of Classification Search
CPC .. A61C 3/04; A61C 5/80; A61C 5/007; A61C 5/30; A61C 7/02; A61C 7/06; A61C 7/08; A61C 7/10; A61C 7/12; A61C 8/0083; A61C 8/0089; A61C 9/0033; A61C 13/12; A61C 15/04; A61C 15/00; A61C 5/82; A61C 5/85; A61C 5/88; A61C 7/36; A61C 5/90; A61M 16/0497; A61M 16/0488; A61M 2039/085; A61M 2210/0625; A61M 2210/0631; A61M 2210/0637; A61M 2209/08; A61F 5/05891; A61F 5/566; A61F 2210/0057; A61F 2250/0007; A61F 2250/0009; A61F 2250/001; A61F 2005/563; A61B 1/00147; A61B 17/24; A61B 2018/00273
USPC ..................... 128/207.14, 861, 859; 604/174
See application file for complete search history.

(56) References Cited

U.S. PATENT DOCUMENTS

| | | | | |
|---|---|---|---|---|
| 1,255,109 | A * | 1/1918 | Russ ...................... | A61C 5/125 433/39 |
| 2,791,030 | A * | 5/1957 | Tofflemire ........... | A61C 17/043 433/138 |
| 4,020,558 | A | 5/1977 | Cournut et al. | |
| 4,217,099 | A * | 8/1980 | Thornton ................. | A61C 7/00 433/148 |
| 4,307,903 | A * | 12/1981 | Wallace ................ | A61M 16/08 128/207.14 |
| 4,641,646 | A * | 2/1987 | Schultz ............. | A61M 16/0463 128/204.18 |

(Continued)

FOREIGN PATENT DOCUMENTS

EP      0860149 B1    9/2002
WO    WO 9639984 A1 * 12/1996  ............... A61C 5/82

*Primary Examiner* — Justine R Yu
*Assistant Examiner* — Matthew D Ziegler
(74) *Attorney, Agent, or Firm* — Loginov & Associates, PLLC; William A. Loginov

(57) ABSTRACT

One or more oral devices having interdental anchors configured to elastically deform and engage with an interdental gap between adjacent teeth. One or more medical devices can then be secured to the oral device via a securing portion, allowing the medical device to be secured relative to the patient.

11 Claims, 14 Drawing Sheets

(56) References Cited

U.S. PATENT DOCUMENTS

| | | | | |
|---|---|---|---|---|
| 4,781,583 | A | * | 11/1988 | Lazarus .................... A61C 5/85 |
| | | | | 433/39 |
| 4,819,636 | A | * | 4/1989 | Gerich ............... A61B 17/3201 |
| | | | | 606/122 |
| 4,968,248 | A | | 11/1990 | McColgan et al. |
| 5,395,343 | A | * | 3/1995 | Iscovich ............... A61M 25/02 |
| | | | | 128/DIG. 26 |
| 2003/0186186 | A1 | * | 10/2003 | Hahn ....................... A61C 5/85 |
| | | | | 433/39 |
| 2004/0197732 | A1 | * | 10/2004 | Sullman ................. A61C 17/08 |
| | | | | 433/94 |
| 2005/0089813 | A1 | * | 4/2005 | Slone ....................... A61C 5/85 |
| | | | | 433/39 |
| 2005/0272005 | A1 | * | 12/2005 | Schaffner ................ A61C 5/88 |
| | | | | 433/149 |
| 2006/0134579 | A1 | * | 6/2006 | Kilcher .................... A61C 5/88 |
| | | | | 433/136 |
| 2006/0240373 | A1 | * | 10/2006 | Amundsen ............... A61C 7/00 |
| | | | | 433/3 |
| 2008/0113315 | A1 | * | 5/2008 | Beggs ....................... A61C 7/00 |
| | | | | 433/149 |
| 2011/0189629 | A1 | | 8/2011 | Kilcher et al. |
| 2011/0250563 | A1 | | 10/2011 | Horvath et al. |
| 2017/0216003 | A1 | * | 8/2017 | Maycher .............. A61C 15/041 |

* cited by examiner

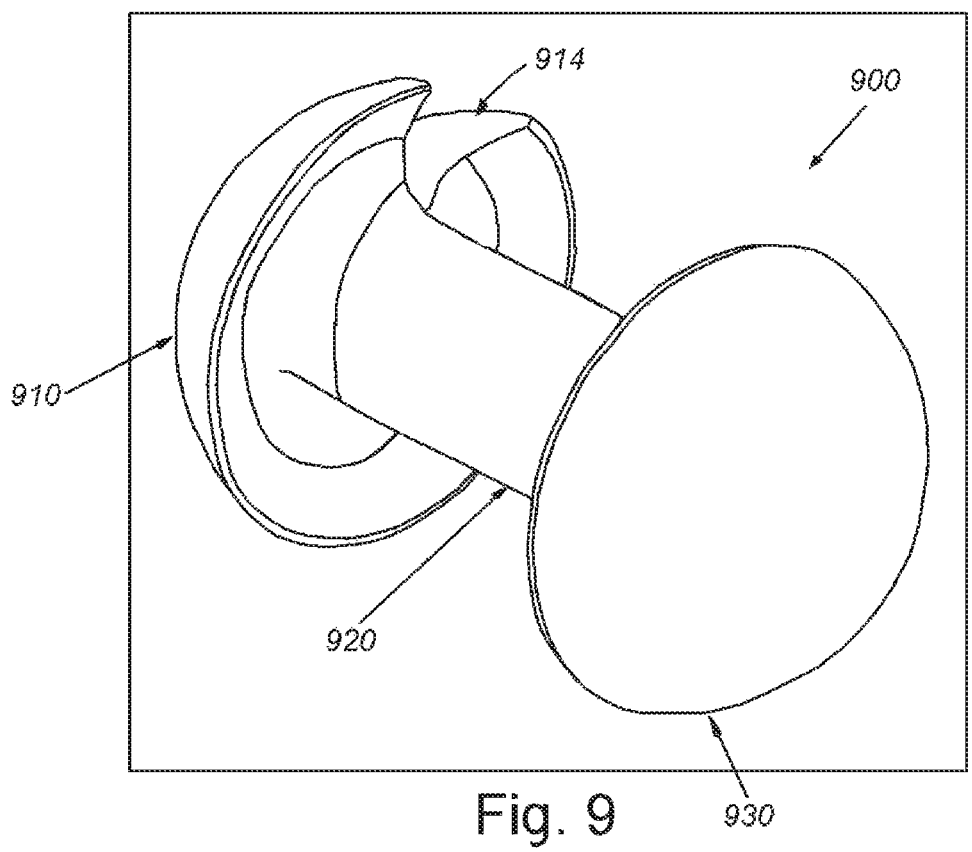

INTERDENTAL ANCHORING APPARATUSES AND METHODS

FIELD OF THE INVENTION

The present application relates to oral devices including interdental anchors.

BACKGROUND OF THE INVENTION

Certain medical procedures require the ability for health care personnel to engage and hold a medical device in place. For example, intubation such as endotracheal intubation, intubation with a transoral laryngeal mask, or nasopharyngeal intubation are all common procedures that require securely fastening a medical device into position.

A common problem associated with tubing is that it can be difficult to keep in place when connected to the patient or otherwise used during a procedure. Proper positioning of tubing is often important, and inadvertent dislodgment can be hazardous or even life-threatening (e.g. inadvertent dislodgement of an endotracheal tube).

Attempts have been made to address the above problem. The conventional technique used to fasten medical devices to patients involves the use of adhesive taping or bandages. This approach has its own shortcomings. Therefore, in the region of the head and neck, tubing is sometimes secured by placing a suture through the oral buccal sulcus mucosa/submucosa and then wrapping it around and tieing it to the perioral tube. In other instances, a circumdental wire is first passed around a tooth, then wrapped around the tube and twisted snugly. Alternatively, another method involves the use of straps, with or without a fastening cuff, that encircle the head or neck of the patient and attach to a tube.

Other medical procedures require the jaw and/or teeth to be generally held in place, e.g., bringing the maxillary and mandibular dentition into approximation either firmly for fracture repair procedures, or more loosely when trying to prevent mandibular retrusion leading to certain forms of sleep apnea. The present approach to placing the maxillary and mandibular dentition into firm occlusal position for surgical indications is with the use of dental arch bars and circumdental wires, or with the use of bone-anchored screws with wires or elastic bands. For individuals with sleep apnea arising from mandibular retrusion, the use of customized or non-customized tooth-borne splints, or the use of continuous positive airway pressure mask/pump are treatment options.

However, these and other attempted solutions have cost and morbidity implications, and risks of discomfort and injury to the patient and health care worker.

SUMMARY OF THE INVENTION

One aspect of the disclosure provides an oral device, comprising: an interdental anchor portion comprising an interior portion, an anchor portion, and an exterior portion, the anchor portion configured to elastically deform from a first state to a second state to engage with an interdental space between two teeth; and a securing portion configured to engage a medical device.

In one example, the interior portion has a width that is greater than the anchor portion.

In one example, the oral device defines a hole and the securing portion defines a plurality of protrusions.

In one example, at least one of the plurality of protrusions are configured to elastically deform to engage with the hole, thereby securing the medical device.

In one example, the medical device comprises a tube.

In one example, the oral device further comprises a post configured to engage with at least one of a plurality of holes defined by the securing portion.

In one example, the elastic deformation increases a length of the anchor portion and decreases a width of the anchor portion.

Another aspect of the disclosure provides a method of installing an oral device, comprising: providing an opposing force on interior portion of an interdental anchor portion relative to an exterior portion; elastically deforming an anchor portion of the interdental anchor portion, thereby altering at least one dimension of the anchor portion; engaging the anchor portion with the altered dimension with an interdental space between two teeth; and releasing the opposing force.

In one example, the method further comprises securing a medical device to a securing portion of the oral device.

In one example, the method further comprises engaging at least one protrusion with at least one hole defined by the oral device.

Another aspect of the disclosure provides an oral device, comprising: an anchor portion configured to elastically deform from a first state to a second state to engage with an interdental space between two teeth; a cap having a distal portion configured to engage with frontal portions of the respective two teeth, the cap defining a cavity between the distal portion and the anchor portion.

In one example, the oral device further comprises a second cap disposed opposite the cap with respect to the anchor portion.

In one example, the second cap comprises a second distal portion configured to engage with lingual or palatal surfaces of the two teeth.

In one example, the second cap defines a second cavity between the second distal portion and the anchor portion.

In one example, the oral device further comprises a base disposed opposite the cap with respect to the anchor portion.

In one example, the cavity is configured to receive an elastic band.

Another aspect of the disclosure provides an oral device system, comprising: a first oral device, comprising: a first anchor portion configured to elastically deform from a first state to a second state to engage with an interdental space between a first tooth and a second tooth; a first cap having a first distal portion configured to engage with frontal portions of the first tooth and the second tooth, the cap defining a cavity between the distal portion and the anchor portion configured to receive an elastic band; and a second oral device, comprising: a second anchor portion configured to elastically deform from a third state to a fourth state to engage with an interdental space between a third tooth and a fourth tooth; a second cap having a second distal portion configured to engage with frontal portions of the second tooth and the third tooth, the second cap defining a second cavity between the second distal portion and the second anchor portion configured to receive the elastic band, thereby anchoring the first oral device to the second oral device via the elastic band.

BRIEF DESCRIPTION OF THE DRAWINGS

The invention description below refers to the accompanying drawings, of which:

FIG. 9 is a perspective view of an oral device according to another aspect of the disclosure;

DETAILED DESCRIPTION

The present application relates to oral devices comprising interdental anchors that can be flossed between adjacent teeth of a mammalian patient (e.g. human).

Figure 1A:
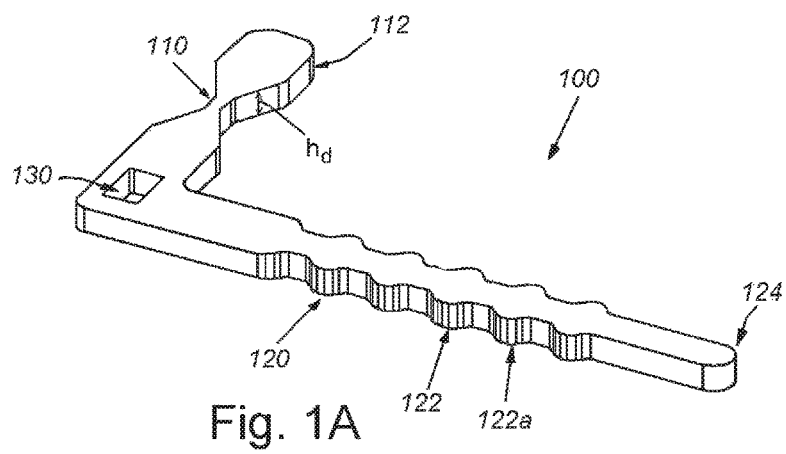
FIG. 1A is a perspective view of an oral device according to one or more aspects of the disclosure.
Figure 1B:
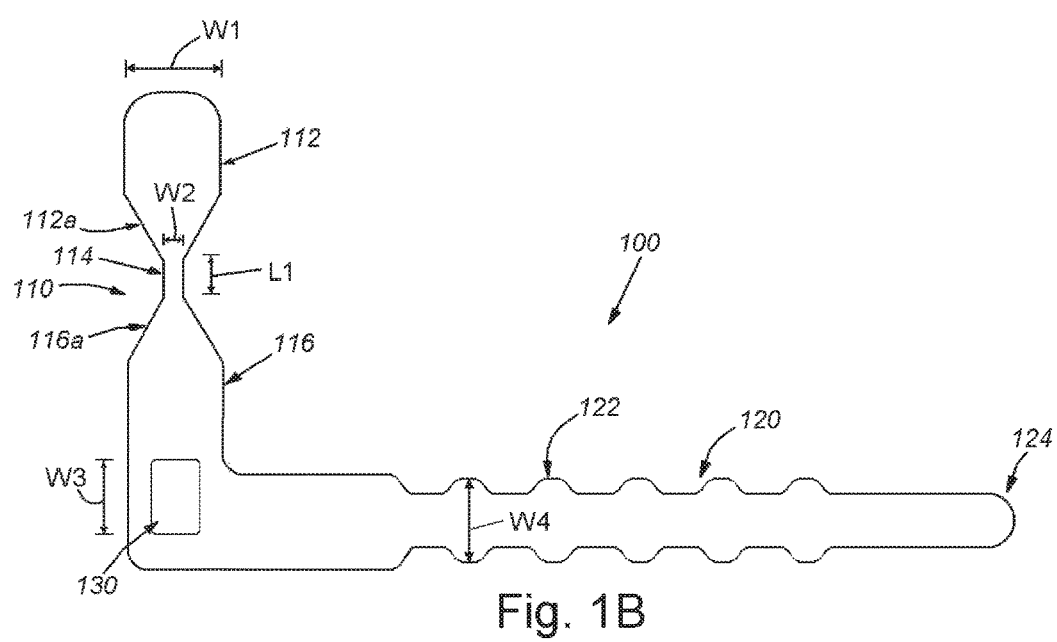
FIG. 1B is a plan view of an oral device according to one or more aspects of the disclosure.

FIG. 1A is a perspective view of an oral device 100 according to one or more aspects of the disclosure. FIG. 1B is a plan view of an oral device 100 according to one or more aspects of the disclosure.

The oral device 100 can be made of any type of material capable of elastically deforming and subsequently returning to its original size and shape, such as a polymer. In one example, the polymer can be silicone, such as Silicon Shore 60A, 70A, or 80A. In another example, the device may incorporate portions that are less compliant such as any of a variety of plastic materials. The oral device 100 can be integrally formed such that it can be molded or cut from a sheet as a single unitary piece (and can have a uniform height $h_1$ as shown in FIG. 1A). In other examples, the oral device 100 can have one or more interconnected parts that can be separately formed.

As shown, the overall body of the oral device 100 can include an interdental anchor portion 110, a securing portion 120, and the body of the oral device 100 can define a hole 130 configured to receive a portion of the securing portion 120.

The interdental anchor portion 110 can include an interior portion 112, e.g., a lingual or palatal portion. As used herein, the terms lingual or palatal refer to a surface of a tooth that is closest or next to your tongue. For the upper teeth, this is called the palatal surface. For the lower teeth, this is called the lingual surface. Further, teeth can refer to natural teeth, dentures, teeth of a human patient, or teeth any of kind of animal patient.

The interior portion 112 can have a first width $w_1$ that can be any width appropriate for the size of a mouth of the mammalian patient. The width $w_1$ can have a range of 6-10 mm, and in one example can have be approximately 8 mm in width, e.g., 8 mm+/−0.5 mm.

The interdental anchor portion 110 can also include an anchor portion 114 (e.g., flossing portion) configured to reside in an interdental gap of the patient. As used herein, "interdental gap" or "interdental space" is used interchangeably with "gingival interdental space" and "gingival dental embrasure," with all terms referring to a space between any two adjacent teeth. The anchor portion 114 can have a width $w_2$ in the range of 1 mm to 2 mm. In one example, the width $w_2$ can be approximately 1.6 mm, e.g., 1.6 mm+/0.15 mm. The anchor portion 114 can have a length $l_1$ in the range of 0.5-5 mm. In one example, the length $l_1$ can be approximately 3 mm, e.g., 3 mm+/−2.5 mm. In addition to the ranges set forth above, the length and width of the anchor portion 140 can vary beyond the above-identified ranges depending on a number of factors, such as the size of the mouth, the size of the tooth, the portion of the mouth in which the oral device 100 will be installed (e.g., incisor, canine, premolar, molar, etc.), variations to the tooth or mouth that may cause interdental spacings vary from other interdental spacings in the same mouth, such as overlapping teeth, or injury, or any other variation that can cause the interdental spacing to be larger or smaller than average.

The interdental anchor portion 110 can also include exterior portion 116, (e.g., a facial portion). As used herein, the term facial can be considered an umbrella term for both buccal and labial. Buccal and labial refer to the tooth surface that faces the outside of a mammal's mouth. For teeth closer to the rear of the mammal's mouth, the tooth surface that is closest or next to the check is called the buccal surface. For teeth that are closer to the front of the mouth, the surface that is closer to the lips is called the labial surface. The exterior portion 116 can have a width substantially similar to the width of the interior portion 112.

The interdental anchor portion 110 can also include an interior transition portion 112a and an exterior transition portion 116a. The interior transition portion 112a comprises a portion of varying with between a width of the interior portion 112 and the width of the anchor portion 114. Similarly, the exterior transition portion 116a comprises a portion of varying width between the exterior portion 116 and the anchor portion 112. In the example of FIGS. 1A and 1B, the interior and exterior transition portions 112a, 116a comprise a linear transition, but other geometric shapes, such as curved or otherwise non-linear transitions are possible.

The body of the oral device can define a hole 130, as mentioned above, to receive a securing portion 120. The securing portion 120 can include one or more protrusions 122 (e.g., notches) configured to pass through and/or engage with the hole 130. In this regard, the hole 130 can have a width $w_3$ in the range of 4-7 mm, and in one example can have a width of approximately 6.3 mm, e.g., 6.3 mm+/−0.1 mm.

The protrusions 122 can have a width $w_4$ in the range of 6-8 mm, depending on the size of the hole 130. In one example, the width of the protrusion 122 can be approximately 7.0 mm, e.g., 7.0+/−0.1 mm. The sizes of the hole 130 and protrusions 122 can be highly variable, and the relative difference in size can be in the range of 0.5 to 1 mm in order to ensure that the protrusions 122 fit through the hole 130 (by elastic deformation), but are not easily returned back through the hole 130 in order to secure a medical device within the securing portion 120. The protrusions 122 can include adjacent planarized surfaces 122a that can assist in preventing the protrusions 122 from returning back through the hole 130.

The length of the securing portion 120, number of protrusions 122, and the pitch spacing therebetween can be highly variable depending on a number of factors, such as the size and shape of the medical device to be secured, the flexibility of the silicone used for the oral device 100, the size and/or shape of the patient's mouth, etc.

As depicted, the interdental anchor portion 110 can be formed at a substantially right angle with respect to the securing portion 120, such that the oral device generally forms an "L" shape. In other examples, the portions 110 and 120 can form acute or obtuse angles with respect to one another.

Figure 2:
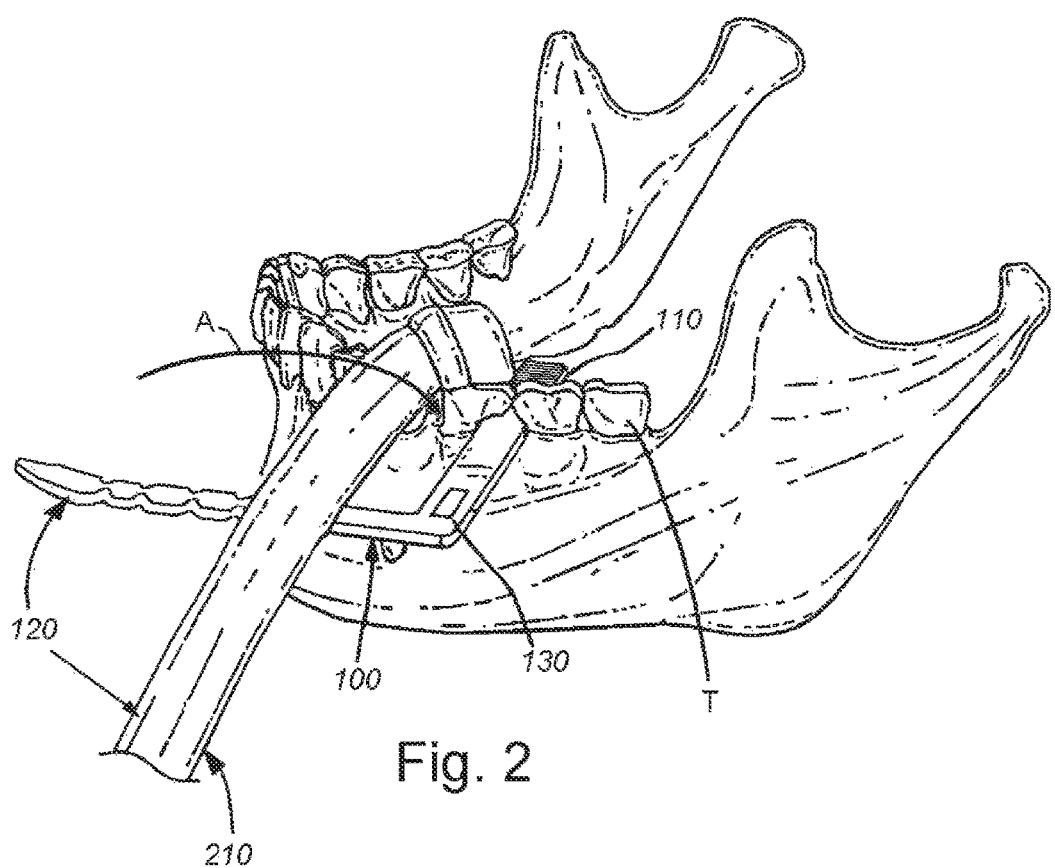
FIG. 2 depicts a jaw of a patient with the oral device of FIGS. 1A-B installed.

FIG. 2 depicts a jaw of a patient with the oral device 100 installed. As shown, the interdental anchor portion 110 is flossed between adjacent teeth T and is secured within the interdental space. Once secured, the securing portion 120 can be wrapped around the medical device 210 (e.g. a tube) as depicted by arrow A and subsequently inserted through the hole 130 until the securing portion 120 fits snugly and securely around the medical device 210. The medical device 210 can be any type of medical device, such as a tube for breathing, a cable for an endoscopic camera, or any other type of medical device.

To install the oral device 100, the medical professional can provide a relative opposing force between the interior and exterior portions 112, 116 so as to elastically deform at least the anchor portion 114. The elastic deformation can include at least one or more of the following deformations: increase in length $l_1$ of the anchor portion 114; decrease in width $w_2$ of the anchor portion 114; and/or decrease in height $h_1$ of the anchor portion 114. This can be accomplished either manually or with an instrument.

In the example depicted, the anchor portion 114 has a generally rectangular cross-section. It is expressly contemplated that the anchor portion 114 can have other geometric configurations and that the elastic deformation can affect the dimensions of those configurations accordingly.

In the manual example, a medical professional may grasp the oral device 100 with one hand on the interior portion 112 and one hand on the exterior portion 116 (or near the hole 130). Once gripped, the medical professional may pull the two portions 112, 116 in opposing directions relative to one another in order to provide the above-mentioned elastic deformation. Once the desired amount of deformation is achieved, the anchor portion 114 can be inserted into the interdental space between two adjacent teeth. This can be achieved based on the decrease in width $w_2$, the overall elasticity of the oral device 100, and the fact that teeth are in close proximity at the level of the cusp, but diverge at the level of adjacent dental cervix. That is, the crown of a tooth has a "waist" that results in the presence of the above-mentioned interdental gap.

Once the anchor portion 114 is positioned correctly within the interdental space, the professional can release the opposing force to allow the oral device 100 to elastically deform back to its original state (e.g., back to $l_1$ and $w_2$). Having returned to its original state, the anchor portion 114 now engages with the adjacent teeth in the interdental space and the gums above or below by a friction fit and is held snugly and securely therewithin.

Once the interdental anchor portion 110 is secured, the securing portion 120 can now be engaged with the medical device. In the example of a tube, the securing portion 120 can be wrapped around to at least partially encircle the medical device. While doing so, the medical professional can feed one or more of the protrusions 122 through the hole 130. The number of protrusions 122 to be fed through the hole 130 depends on the length of the securing portion 120 as well as the overall size (or caliber) of the medical device to be secured. The medical professional can begin by feeding the distal portion 124 of the securing portion 120 through the hole 130. Since the distal portion 124 has no protrusions 122, this section is easily fed through the hole 130 and can be gripped on the other side once fed through. Once the first protrusion 122 approaches the hole 130, the distal portion 124 can be pulled with sufficient force to elastically deform the protrusion 122 (e.g., reduce the width w4) such that the protrusion 122 can be fed through the hole 130. Once the protrusion 122 is fed through the hole 130 and reaches the other side, the protrusion 122 returns to is original state and will now require a similar force to be removed the hole 130. Absent such force, the securing portion 120 can be formed into in a closed loop that secures the medical device in place relative to the patient's mouth. This process can be repeated until the desired length of securing portion is encircled around the medical device.

To remove the securing portion 120 from engagement with the hole 130, the securing portion 120 can be pulled out of the hole 130 with sufficient force to again elastically deform the protrusions 122, allowing them to return back through the hole 130. This can be repeated until all protrusions 122 are removed from the hole 130 and the medical device can be removed.

To remove the interdental anchor portion 110, an opposing force can be applied with respect to the portions 112 and 116 to elastically deform the anchor portion 114 to a reduced width such that it can be disengaged with from the interdental space.

Figure 3:
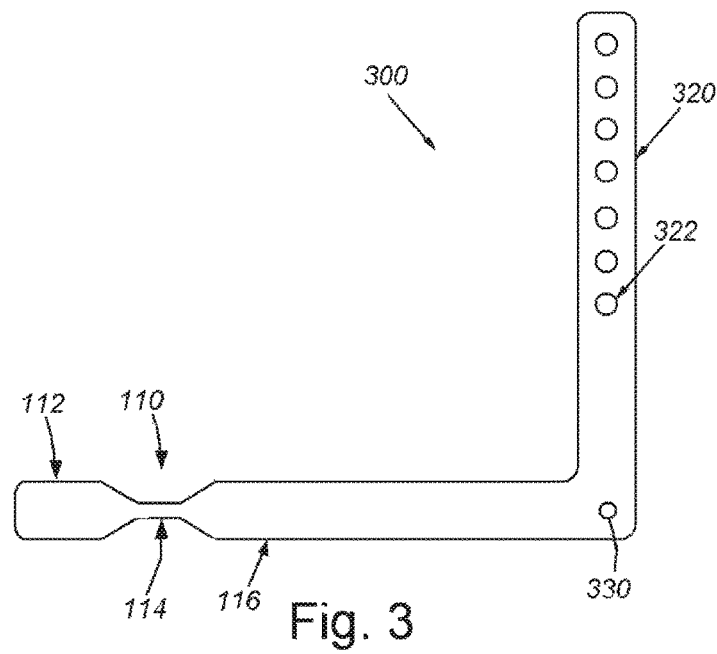
FIG. 3 depicts an oral device according to another aspect of the disclosure.

FIG. 3 depicts an oral device 300 according to another aspect of the disclosure. In this example, the interdental anchor portion 110 can be substantially similar to the example set forth in FIGS. 1A-B. In this example, however, the securing portion 220 can define a plurality of holes 222 and the oral device 300 can include a post 330. The post 330 can have a dimension (e.g., diameter) greater than a dimension (e.g., diameter) of the holes 322 such that at least one of the holes 322 can be pressed onto the post and elastically deformed to engage therewith. Once engaged, the securing portion 320 can securing a medical device therein similar to the example set forth above.

Figure 4:
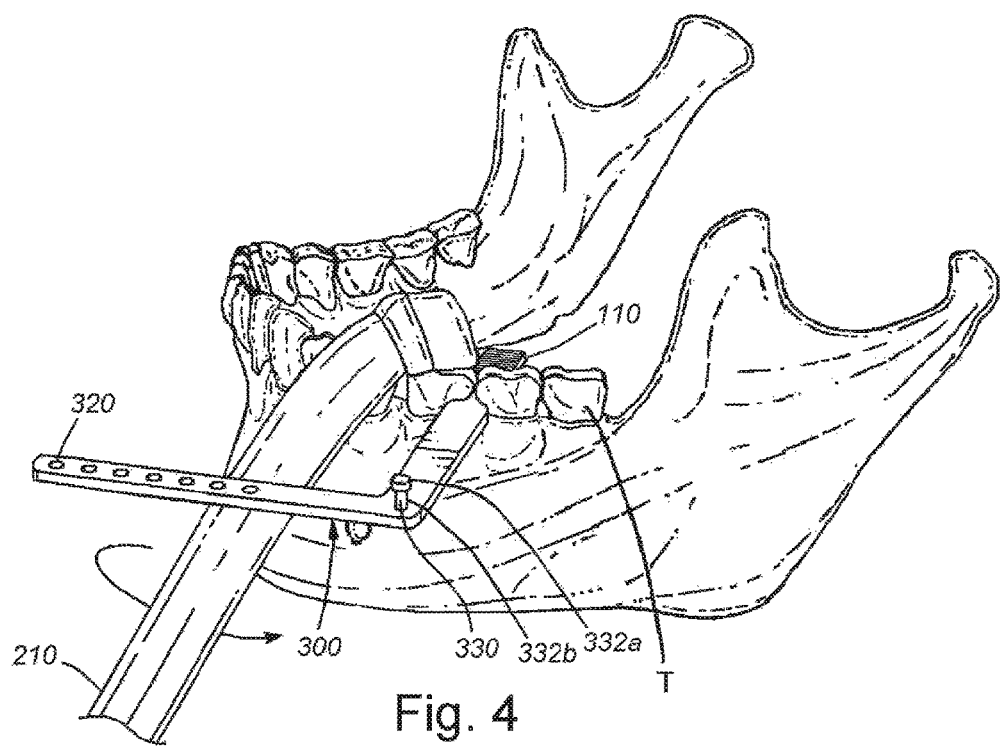
FIG. 4 depicts the oral device of FIG. 3 in operation.

FIG. 4 depicts the oral device of FIG. 3 in operation. As shown, the interdental portion 110 is engaged in the interdental space between two adjacent teeth (as is described above with respect to FIG. 2). The securing portion 320 can wrap around or encircle the medical device 210 (e.g., tube) so as to secure the medical device 210 relative to the mouth of the patient. The securing portion 320 can be wrapped around the medical device such that one of the holes 322 engages with the post 330. As shown, the post 330 has a thick section 332a and a thinner section 332b, with the thick section have a greater diameter (or any other dimension) than the thinner section. One of the holes 322 can plastically deform to fit around the thick section and be secured on the thin portion, thereby securing the medical device in place.

Figure 5A:
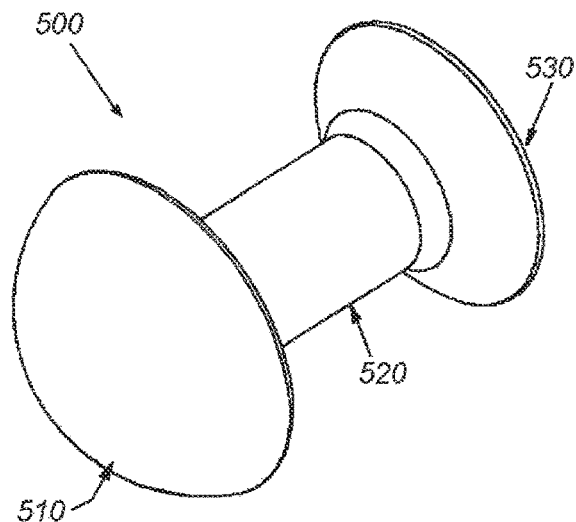
FIG. 5A is a perspective view an oral device according to another aspect of the disclosure.
Figure 5B:
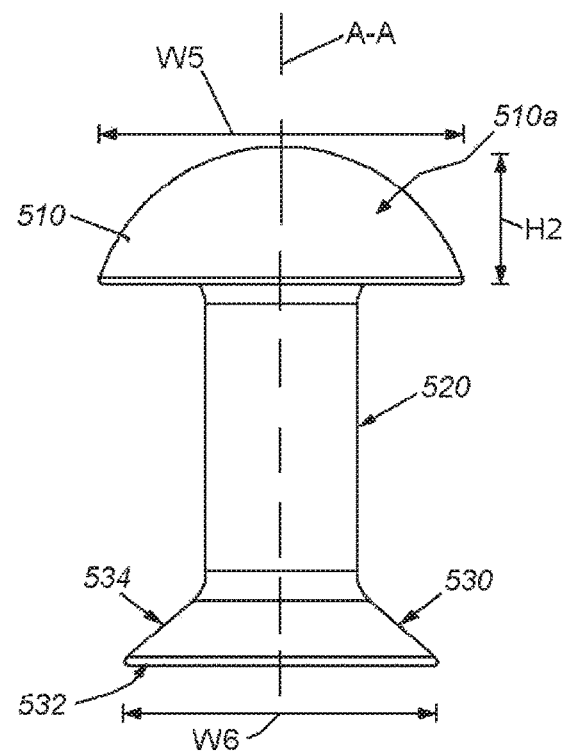
FIG. 5B is a side view of the oral device of FIG. 5A.
Figure 5C:
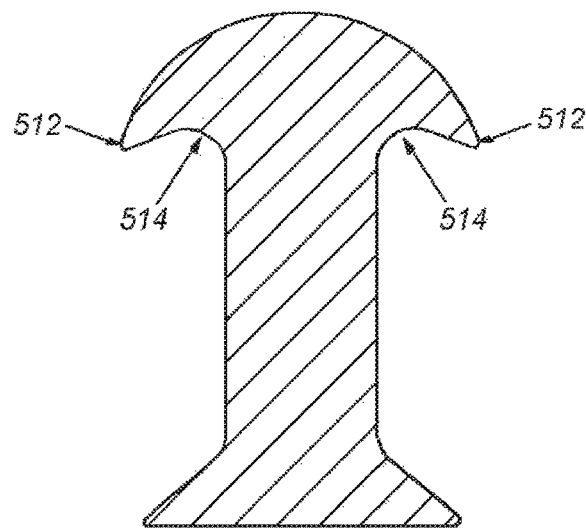
FIG. 5C is a cross section of the oral device of FIGS. 5A-B along the line A-A.
Figure 6:
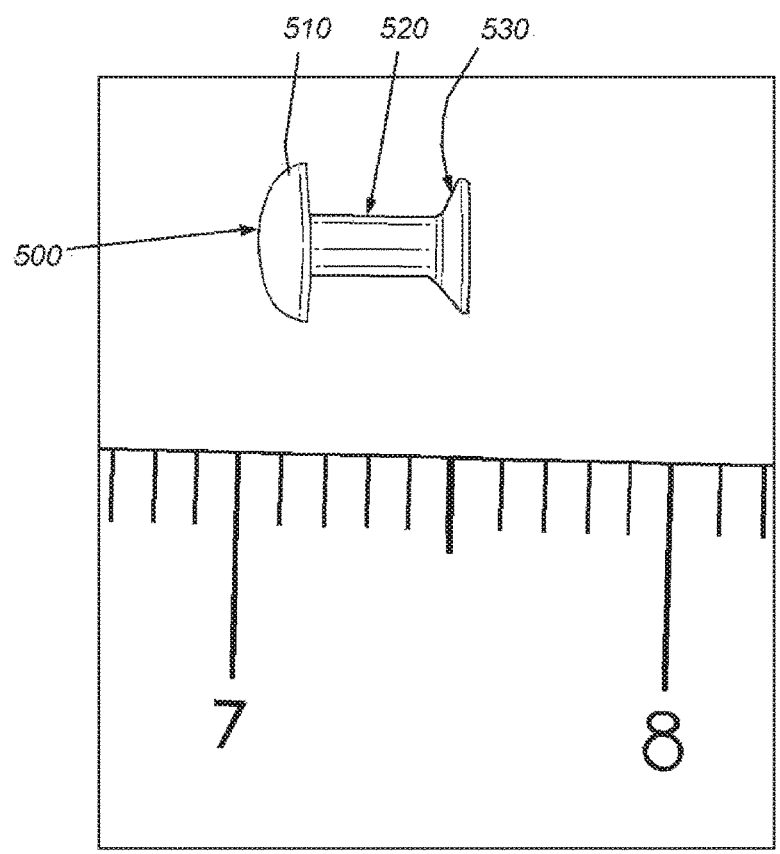
FIG. 6 is a side view of the oral device of FIGS. 5A-C with a ruler (cm) for scale.

FIG. 5A is a perspective view an oral device according to another aspect of the disclosure. FIG. 5B is a side view of the oral device of FIG. 5A. FIG. 5C is a cross section of the oral device of FIGS. 5A-B along the line A-A. FIG. 6 is a side view of the oral device of FIGS. 5A-C with a ruler (cm) for scale.

The oral device 500 can be made of any type of material capable of elastically deforming and subsequently returning to its original size and shape, such as a polymer. In one example, the polymer can be silicone, such as Silicon Shore 60A, 70A, or 80A. The oral device can be integrally formed such that it can be molded or cut from a sheet as a single unitary piece or it can have one or more interconnected parts that can be separately formed.

As shown, the oral device 500 includes a cap 510, an anchor portion 520 (e.g., flossing portion), and a base 530. A top surface 510a of the cap 510 can be a substantially spherical cap (e.g., a portion of a sphere cut off by a plane) having a height $h_2$ in the range of 1-2 mm and a width $w_5$ in the range of 2-4 mm when viewed from the side. The cap 510 can have a radius of curvature thereby defining a "mushroom" shape to the cap.

The flossing or anchor portion 520 can be substantially cylindrical such that it has a circular cross section and a radius in the range of 1-2 mm. In one example, the radius can be approximately 1.6 mm, e.g., 1.6 mm+/−0.5 mm. In other examples, the cross section of the anchor portion can be substantially elliptical such that it has a major axis that is greater in dimension than a minor axis.

The base 530 can have a width $w_6$ in the range of 2-3 mm that can be less than or equal to the width of the cap and can have a planar surface 532. The base can include a transition portion 534 that transitions between the planar surface 532 and the anchor portion 520.

As shown in FIG. 5C, the cap can define a radial cavity 514 defined between the distal portion 512 of the cap and the anchor portion 520. The radial cavity 514 is at least partially vertically recessed within the cap 510 such that at least a portion of the radial cavity extends above the distal portion 512 with respect to the base 530. The radial cavity can itself be curved such that it defines a radius of curvature.

The oral device 500 can be installed manually by a medical professional, can be installed with an instrument, or can include attachment features (as will be described in detail below). During manual installation, a medical professional may provide an opposing force relative to the cap and the base, thereby elastically deforming the anchoring portion 520. The elastic deformation can include a decrease in radius and diameter (in the example of a circular cross section). In the example of the elliptical cross section, the major axis diameter may increase while the minor axis may increase (or vice versa). This elastic deformation allows the anchoring portion to be inserted into the interdental space of a patient. In the elliptical example, the anchor portion 520 can be inserted with the major axis positioned vertically in the interdental space and subsequently rotated such that the major axis is disposed horizontally with respect to adjacent teeth.

Once positioned in the interdental space, the opposing force can be removed and the oral device 500 can return to its original state, with the anchor portion 520 providing a friction fit in the interdental space and thereby securing the oral device between two teeth in the mouth. Once returned to its original state, the base 530 can fit snugly against the lingual or palatal surfaces of the adjacent teeth while the distal portion 512 of the cap can fit snugly against the facial portion of the adjacent teeth. This configuration results in the cavity 514 being formed and at least partially or completely enclosed between the distal portion and the facial portion of the tooth. Once engaged, a portion of an elastic band (not shown) can be engaged with the cavity. This process can be repeated over a plurality of teeth, such that the patient's mouth can include a plurality of oral devices installed therein and the oral devices can be secured to one another by elastic bands, thereby securing the teeth, mouth, and/or jaw in place.

For example, oral devices can be placed in adjacent interdental gaps on the lower teeth and/or can be placed on interdental spaces on the lower and upper jaws. Elastic bands could first be applied to the anchors on the lower jaw (horizontally) on either the lingual/palatal side and/or the labial side, before placing the maxillomandibular bands (vertically) in order to prevent anchor dislodgment.

Figure 8:
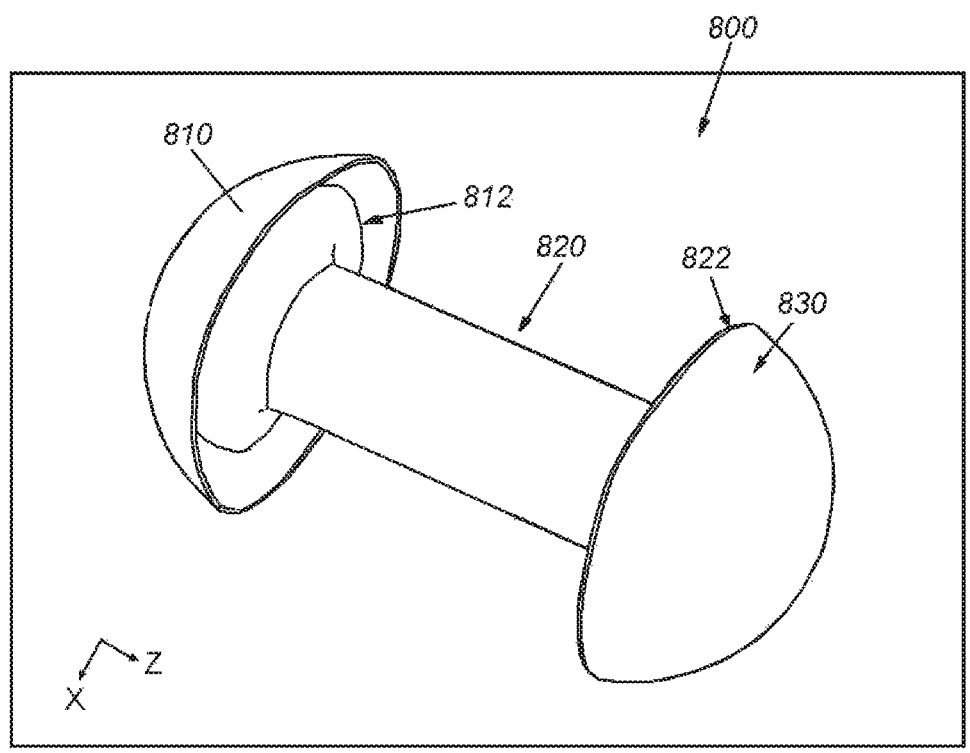
FIG. 8 depicts a double-capped oral device according to one or more aspects of the disclosure

Although the examples of FIG. 5A-C depict an oral device 500 with a cap 510 and a base 530, another example of the present application includes an oral device having a second cap instead of the base 530 (e.g., a double-capped oral device, as depicted in FIG. 8).

Figure 7A:
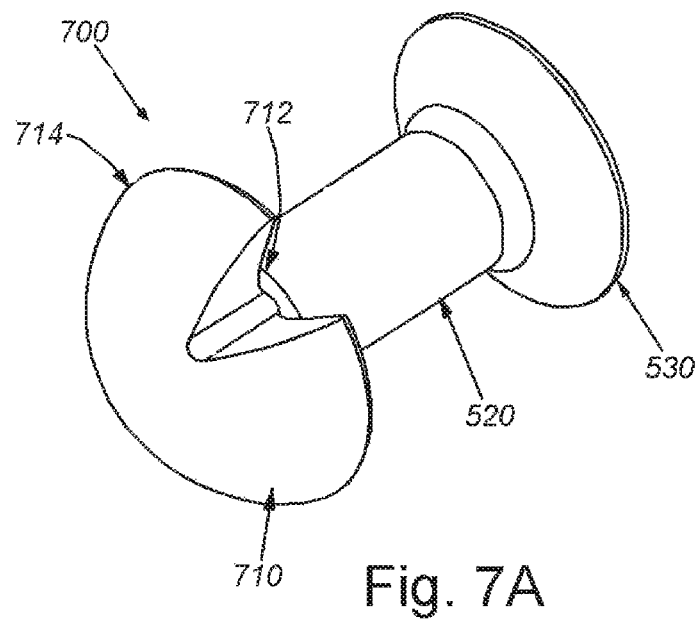
FIG. 7A is a perspective view an oral device according to another aspect of the disclosure.
Figure 7B:
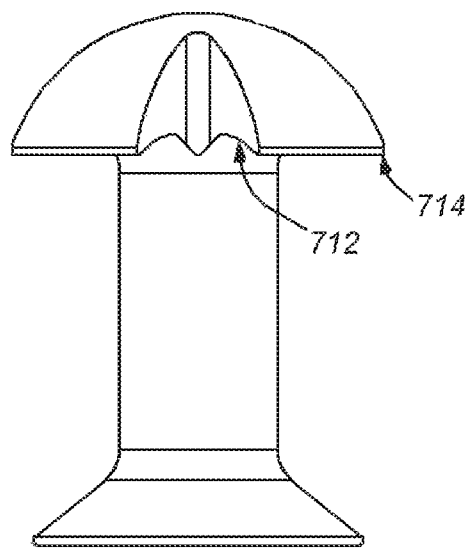
FIG. 7B is a side view of the oral device of FIG. 7A.
Figure 7C:
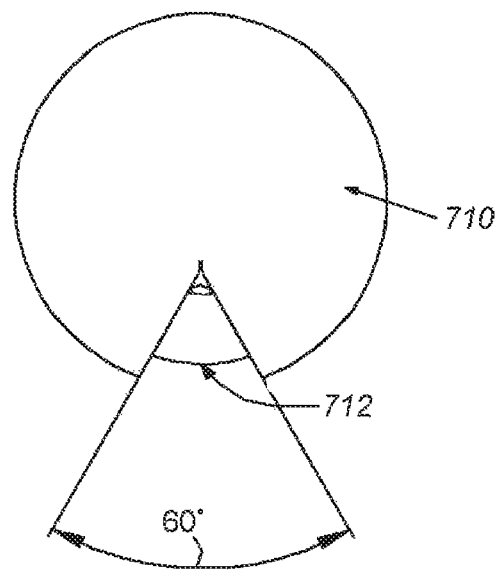
FIG. 7C is a top view of the oral device of FIGS. 7A-B.

FIG. 7A is a perspective view an oral device according to another aspect of the disclosure. FIG. 7B is a side view of the oral device of FIG. 7A. FIG. 7C is a top view of the oral device of FIGS. 7A-B.

The anchor portion 520 and base portion 530 are substantially similar to the example set forth in FIGS. 5A-C. In this example, the cap 710 defines a cutout 712. As shown in FIGS. 7B-C, the cutout 712 can be triangular (when viewed from above) and can extend between the distal portion 714 and a central axis C of the oral device 700. An angle formed by the cutout can be any angle in the range of 45-90 degrees, and in one example defines an angle of 60 degrees.

During installation, the cutout 712 provides the medical professional an entry point for inserting the elastic band into the cavity.

FIG. 8 depicts a double-capped oral device 800 according to one or more aspects of the disclosure. In this example, the first cap 810 and second cap 830 can be secured on interior and exterior portions of the teeth and elastic bands can be installed on either side of the tooth, with the anchor portion 820 being flossed between adjacent teeth. Each of the caps 810 and 830 can define cavities 812 and 822 (not shown) for receiving an elastic band.

In another example, the double-capped device can include a longer anchor portion that can be engaged with two adjacent interdental spaces simultaneously such that both caps face outward. The 'double-capped' anchor would therefore have an identical mushroom cap on both ends and the two caps would face labially out from two adjacent gingival embrasures. This configuration can add stability and prevent dislodgment during the tight fixation of upper-to-lower jaw with orthodontic elastic bands.

FIG. 9 is a perspective view of an oral device according to another aspect of the disclosure. In this example, oral device includes two caps 910 and 930 and an anchor portion 920. In this example, the cap 910 defines a cutout portion 914 while the cap 930 is identical to the cap 510.

Figure 10A:
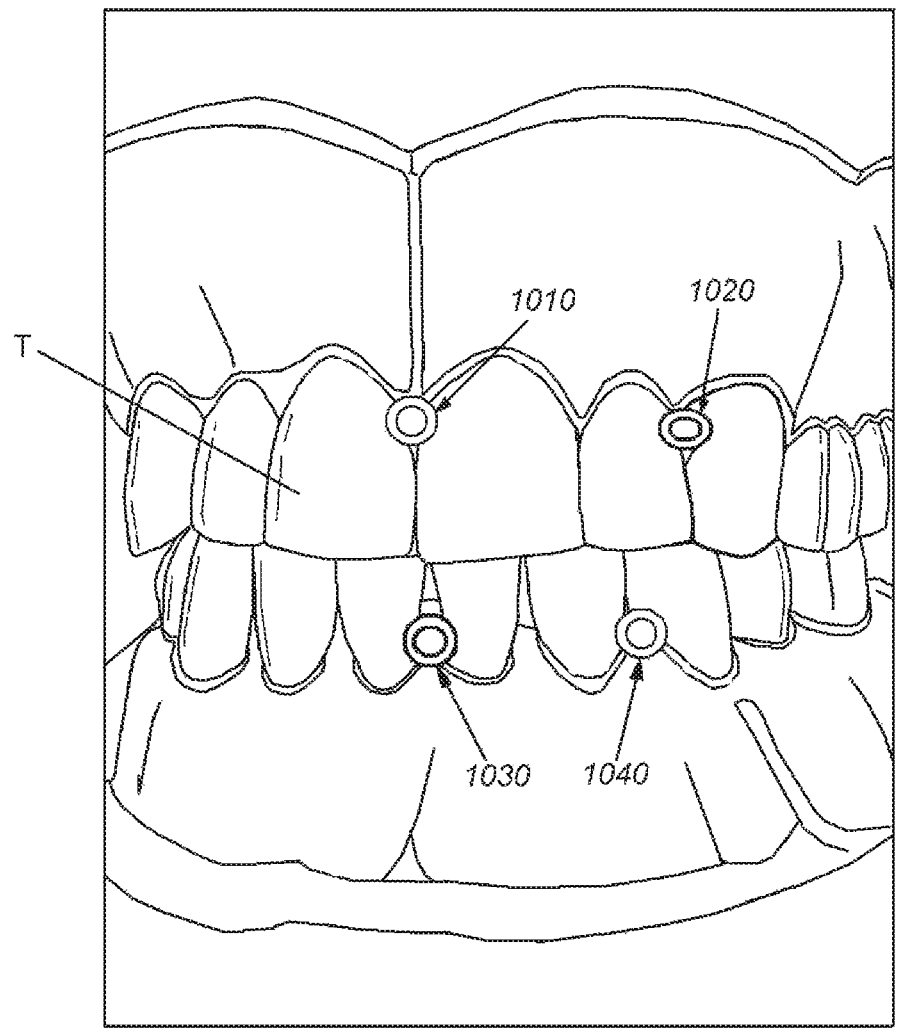
FIG. 10A is a front view of a patient with a plurality of oral devices installed between teeth.

FIG. 10A is a front view of a patient with a plurality of oral devices 1010-1040 installed between teeth T. As shown, the caps of the oral devices 1010-1040 can face outward to allow for installation of elastic bands (not shown). For example, an elastic band can be connected from band 1010 to band 1020 and another from band 1010 to band 1040. Any combination of elastic band connections is contemplated based on the desired configuration of oral devices.

Figure 10B:
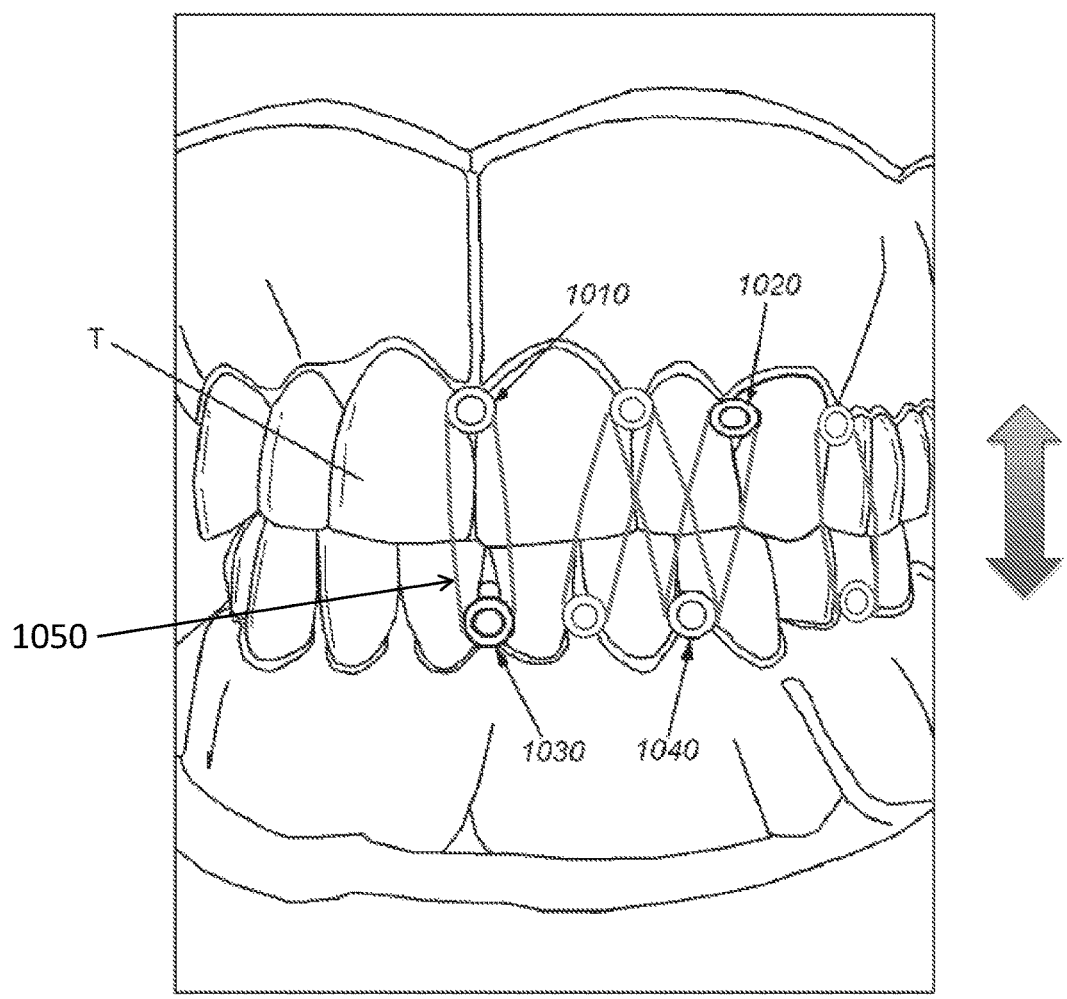
FIGS. 10B-D depict several examples of elastic band arrangements according to one more examples of the disclosure
Figure 10C:
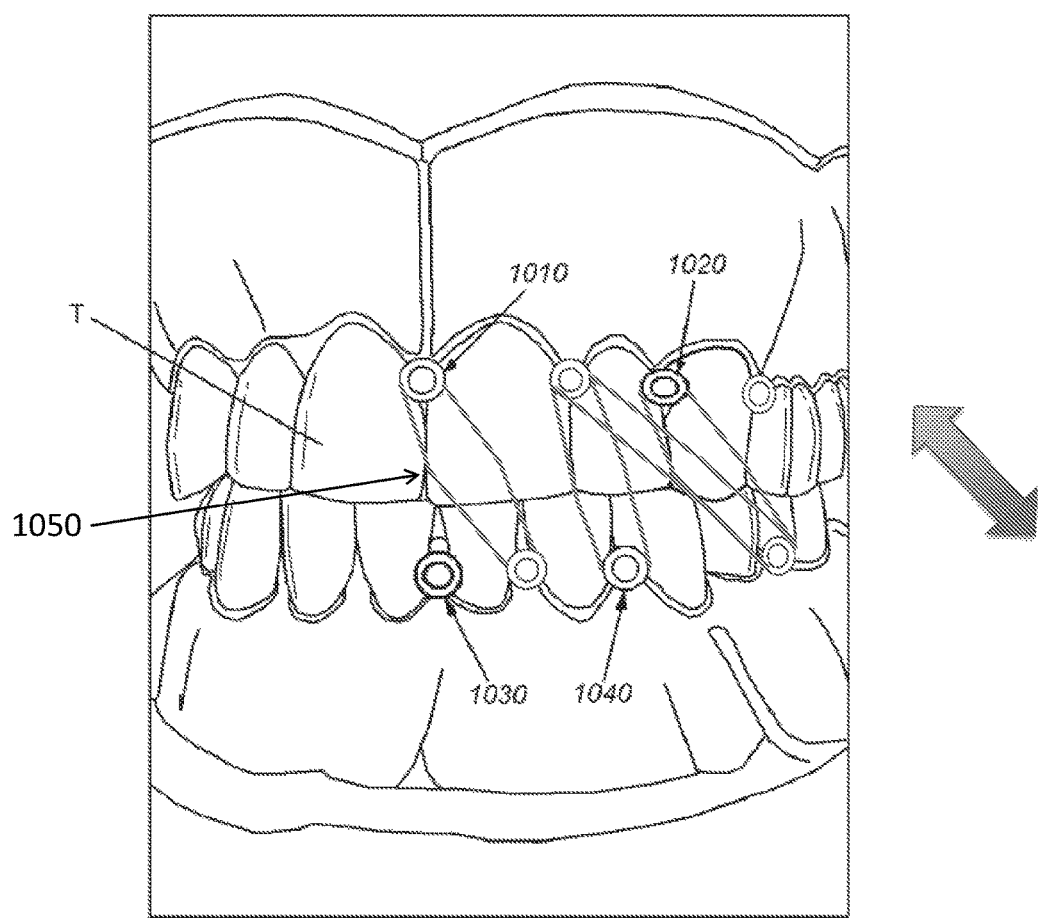
Figure 10D:
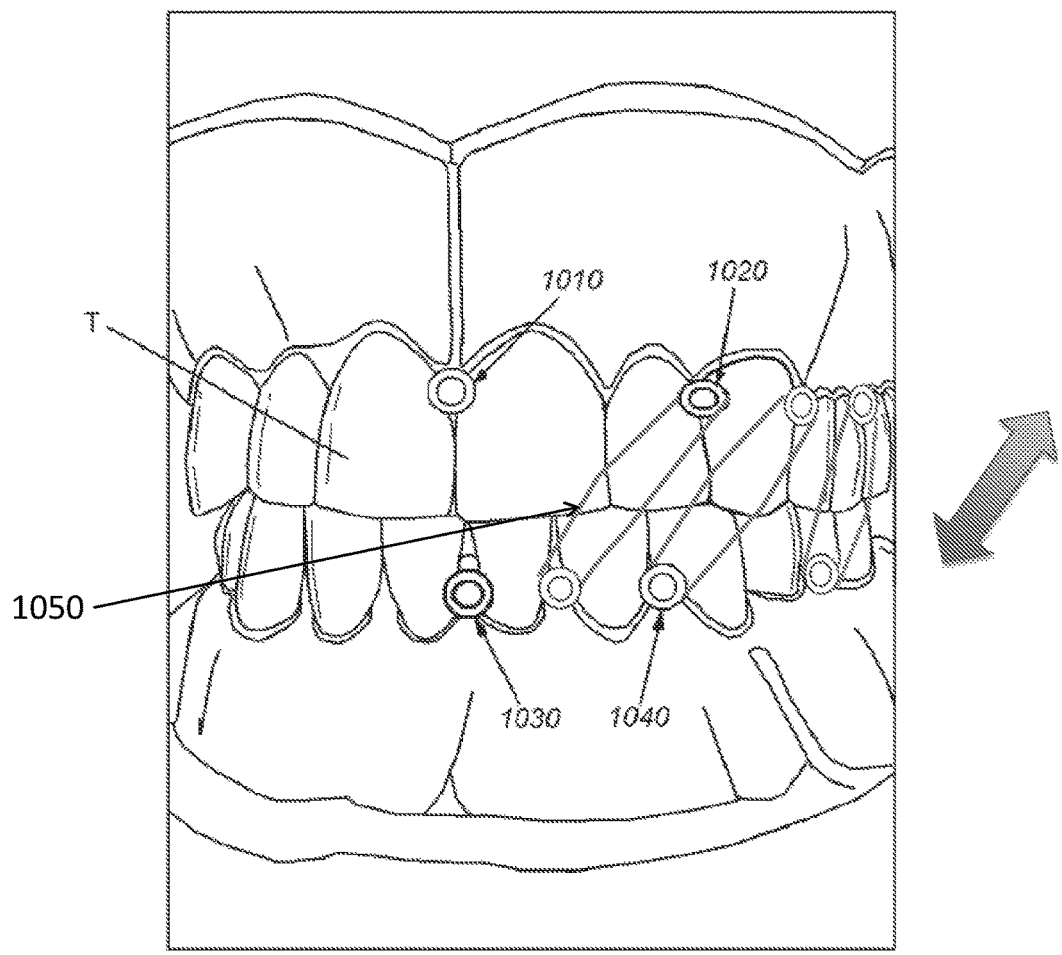

FIGS. 10B-D depict several examples of elastic band arrangements according to one more examples of the disclosure. A number of elastic bands 1050 can be placed ranging from a single one centrally, one on either side, to many placed bilaterally, depending on the requirements. During repair of a mandibular and/or maxillary fracture, the rubber bands may be placed in a more upright (vertical) orientation in order to encourage a firm occlusal position ("maxillomandibular fixation=MMF"), as shown in FIG. 10B.

In other circumstances, the objective may be to shift the mandible forward (for example, in preventing mandibular retrusion during sleep to prevent sleep apnea) or the maxilla posteriorly (ex. post-operatively in a situation where the occlusion requires some fine adjustment). This can be achieved by placing the elastic bands on the anchors in an oblique vector (as generally indicated by the arrows) as demonstrated in FIGS. 10C and 10D.

Figure 11:
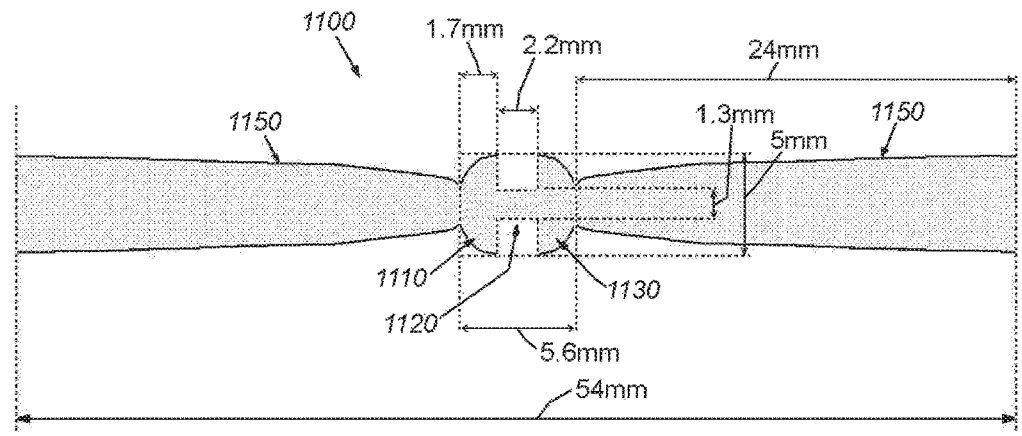
FIG. 11 is a schematic diagram of an oral device with attachment features according to another aspect of the disclosure.

FIG. 11 is a schematic diagram of an oral device with attachment features according to another aspect of the disclosure. As shown, the oral device 1100 can include end caps and an anchor portion 1120. In order to facilitate elastic deformation, removable attachment features 1150 can be removably, semi-permanently, or permanently attached to the end caps 1110 and 1130.

Figure 12:
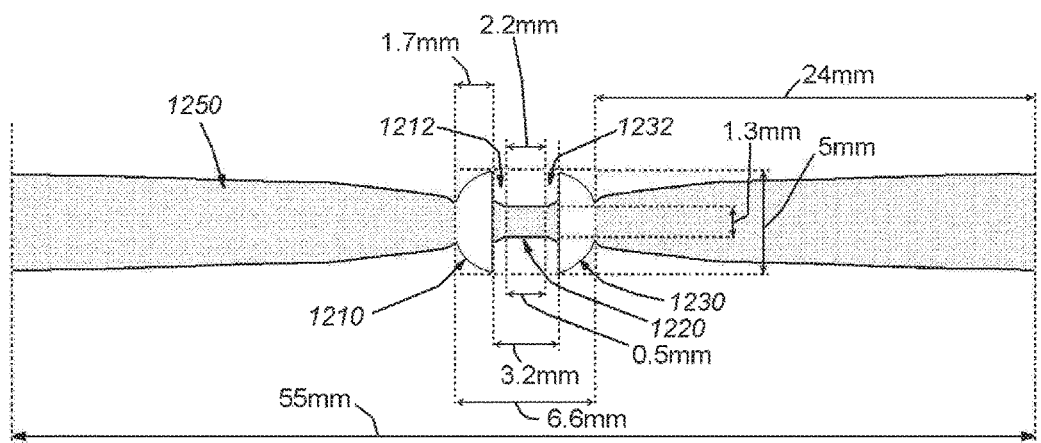
FIG. 12 is a schematic diagram of an oral device with attachment features according to another aspect of the disclosure.

FIG. 12 is a schematic diagram of an oral device with attachment features according to another aspect of the disclosure. As shown, the oral device 1200 can include end caps and an anchor portion 1220. In order to facilitate elastic deformation, removable attachment features 1250 can be removably, semi-permanently, or permanently attached to the end caps 1210 and 1230. One or both of the caps 1210 and/or 1230 can define the radial cavity (as described above with respect to FIG. 5 and elements 512 and 514) defined between the distal portions 1212 and/or 1232 of the caps and the anchor portion 1220.

Figure 13:
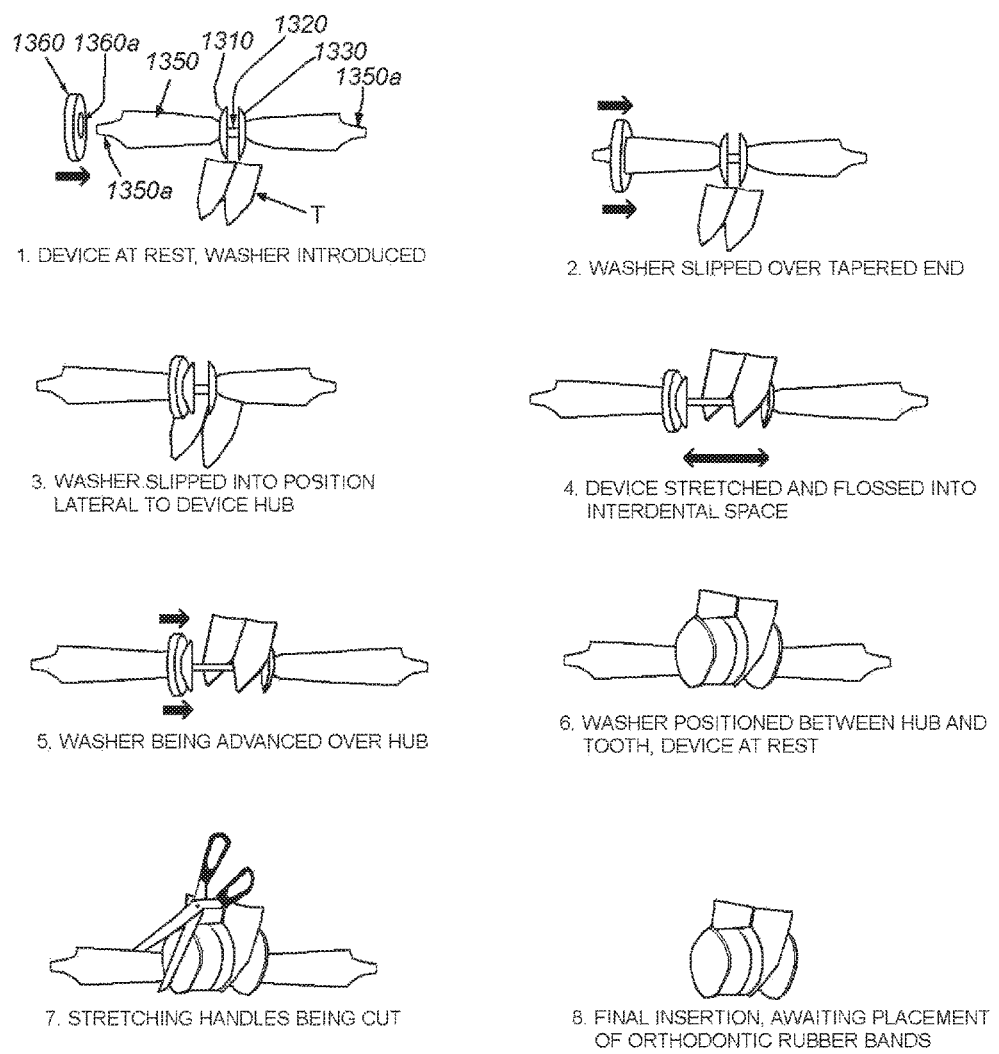
FIG. 13 depicts various stages of installation of the oral device of FIG. 11 or 12 according to one or more aspects of the disclosure.

FIG. 13 depicts various stages of installation of the oral device of FIG. 11 or 12 according to one or more aspects of the disclosure. As shown, the oral device 1300 can include a pair of caps and 1310, 1330 and an anchor portion 1320 to be flossed between adjacent teeth T. The oral device 1300 can also include attachment features 1350 with tapered ends 1350a for use during installation. Optionally, a washer 1360 may also be provided, as will be described in detail below. The washer can be formed of a polymer similar to the oral device above, e.g., medical silicone, high durometer, firm but gentle against the teeth. In another example, the washer can be fabricated out of silicone or some other compatible elastic material. In one particular example, the washer can have a stainless steel ring along an outer surface so that instead of using elastic bands (as shown in FIGS. 10B-D), fine surgical wire (26 G or 25 G) could be used to achieve MMF as is commonly done with conventional stainless steel arch bars and wires.

The washer 1360 may be slipped over the tapered end 1350a of the attachment feature 1350 toward the oral device 1300 until it is adjacent to a surface of the cap 1310 facing away from the anchor portion 1320. A medical professional may then grip the attachment features 1350 (or the tapered ends 1350a) and provide an opposing force to cause elastic deformation of the anchor portion 1320, as shown at stage 4. Once the deformed anchor portion is flossed between adjacent teeth, the washer 1360 may be advanced over the cap 1310 such that the anchor portion 1320 is disposed within a central hole 1360a defined in the washer 1360. The medical professional may then release the opposing force, allowing the anchor portion to deform and the caps 1310, 1330 and washer 1360 to be secured. In this example, the washer can be secured against the labial or inside surface of the teeth. The attachment features 1350 can be removed, for example, by cutting, perforation, or any other such removal method. Once removed, elastic bands may be secured to the oral device 1300 as described above.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. Accordingly, this description is meant to be taken only by way of example, and not to otherwise limit the scope of this invention.

The invention claimed is:

1. An oral device for engaging a medical device, comprising:
    an interdental anchor portion comprising an interior portion, an anchor portion, and an exterior portion, the anchor portion configured to elastically deform from a first state in which the anchor portion has a first length to a second state in which the anchor portion has a second length, the second length being greater than the first length, the second state adapted to be positioned in an interdental space and be engaged with two teeth, the interior portion and the exterior portion having a width that is greater than the anchor portion in the first state and in the second state; and
    a securing portion configured to engage the medical device by wrapping around the medical device and holding the medical device in a fixed location relative to the teeth, the securing portion being unitary with the anchoring portion, and the securing portion being an elongated strip configured to be wrapped around the medical device and secured to the oral device, thereby encircling the medical device and securing the medical device to the mouth of the patient.

2. The oral device of claim 1, wherein the oral device defines a hole and the securing portion defines a plurality of protrusions.

3. The oral device of claim 2, wherein at least one of the plurality of protrusions are configured to elastically deform to engage with the hole, thereby being adapted to secure the medical device.

4. The oral device of claim 1, further comprising a post configured to engage with at least one of a plurality of holes defined by the securing portion.

5. The oral device of claim 1, wherein the elastic deformation increases a length of the anchor portion and decreases a width of the anchor portion.

6. The oral device of claim 1, further comprising a medical device.

7. The oral device of claim 6, wherein the medical device comprises a tube.

8. The oral device of claim 1, wherein the interdental anchor portion is made of a silicone.

9. The oral device of claim 1, wherein the securing portion is unitary with the anchoring portion, and the securing portion and the anchoring portion are made of silicone.

10. A method of installing an oral device, comprising:
    providing an oral device having an interdental anchor portion, an exterior portion, an interior portion, an anchor portion, and a securing portion: applying an opposing force on an interior portion of an interdental anchor portion relative to an exterior portion; elastically deforming the anchor portion of the interdental anchor portion, thereby increasing a length of the anchor portion and decreasing a width of the anchor portion; engaging the anchor portion with the increased length and decreased width with an interdental space between two teeth; securing the oral device to the patient by releasing the opposing force, thereby increasing the width of the anchor portion so that the anchor portion becomes anchored between the teeth of the patient; and wrapping the securing portion around a medical tube and attaching a distal portion of the securing portion to the oral device in order to secure the medical tube to the oral device, whereby the medical tube is secured to the oral device, and the oral device is anchored to the patient, so that the medical tube is secured to the patient.

11. The method of claim 10, further comprising engaging at least one protrusion of the securing portion with at least one hole defined by the oral device.

\* \* \* \* \*